United States Patent [19]

Yachi et al.

[11] Patent Number: 4,990,454

[45] Date of Patent: Feb. 5, 1991

[54] YH206 CELL LINE AND MONOCLONAL ANTIBODY PRODUCED BY IT

[75] Inventors: Akira Yachi; Kohzoh Imai; Takao Endo; Yuji Hinoda; Takafumi Yamashita; Hideo Fujita, all of Sapporo, Japan

[73] Assignee: Nihon Medi-Physics Co., Ltd., Hyogo, Japan

[21] Appl. No.: 463,810

[22] Filed: Jan. 12, 1990

Related U.S. Application Data

[63] Continuation of Ser. No. 798,276, Nov. 12, 1985, abandoned.

[51] Int. Cl.$^5$ .................. C12N 5/00; A61K 35/14; C07K 3/00; C07K 15/00
[52] U.S. Cl. ........................... 435/240.27; 530/387; 530/808; 530/809; 424/85.8
[58] Field of Search ................. 435/240.27; 530/387, 530/808, 805; 424/85.8

[56] References Cited

U.S. PATENT DOCUMENTS 4,683,200  7/1987  Hirohashi et al. ................. 435/68

OTHER PUBLICATIONS

Endo, T. et al., "Preparation of a Monoclonal Antibody to Human Lung Adenocarcinoma Cells and Detection of Corresponding Antigen(s) in Sera of Malignant Diseases", Sapporo Med. J., vol. 54, No. 4, pp. 393–410, Oct., 1985.

Iguro, T. et al., "Sialylated Lewis* Antigen Detected in the Sera of Cancer Patients", The Lancet, vol. II, pp. 817–818, Oct. 6, 1984.

Vark, N. M. et al., "Antigens Associated with a Human Lung Adenocarcinoma Defined by Monoclonal Antibodies", Cancer Research, vol. 44, pp. 681–687, Feb., 1984.

Zimmer, A. M. et al., (I) "Radioimmunoscintigraphy of Human Lung Adenocarcinoma with Iodine-131 Tumor-Specific Monoclonal Antibody", 4th Annual Congress for Hybridoma Research, San Francisco, Calif., U.S.A., Feb. 3–6, 1985, Hybridoma, vol. 4, No. 1, p. 72, 1985.

Zimmer, A. M. et al. (II), "Radioimmunoscintigraphy of Human Lung Adenocarcinoma with $^{131}$I Tumor-Specific Monoclonal Antibody", 30th Annual Meeting of the Society of Nuclear Medicine (Central Chapter), Chicago, Ill., U.S.A., Mar. 21–23, 1985. J. Nucl. Med., vol. 26, No. 6, p. 675, 1985.

Lee, I., et al., "Immunohistochemical Staining of Various Lung Carcinoma Types with Monoclonal Antibody 443A-6", 42nd Annual National Meeting of the American Federation for Clinical Research, Washington, D.C., May 3–6, 1985.

Clin. Res., vol. 33, No. 2, Part 1, p. 454A, 1985.

Radosevich, J. A., "Monoclonal Antibody 44-3A6 as a Probe for a Novel Antigen Found on Human Lung Carcinomas with Glandular Differentiation", Cancer Research, vol. 45, pp. 5808–5812, Nov., 1985.

Endo, T. et al., Report of General Meeting of Japan Immunological Association, vol. 14, 123 (P. 572), "Preparation of Monoclonal Antibody to Human Lung Adenocarcinoma Cells", (Nov. 10, 1984).

Primary Examiner—Margaret Moskowitz
Assistant Examiner—Thomas M. Cunningham

[57] ABSTRACT

A monoclonal antibody specifically reactive to a human adenocarcinoma cell, which is obtainable by cultivating a fused cell obtained by fusing a mammalian animal cell, immunized with a human adenocarcinoma cell, with a myeloma cell.

2 Claims, No Drawings

YH206 CELL LINE AND MONOCLONAL ANTIBODY PRODUCED BY IT

This application is a continuation of application Ser. No. 06/798,276, filed Nov. 12, 1985, abandoned.

The present invention relates to a monoclonal antibody, and its preparation and use. More particularly, it relates to a novel monoclonal antibody specifically reactive to a specific antigen in human adenocarcinoma cells or leaked out therefrom into blood, a process for preparing said monoclonal antibody by cultivation of hybridoma cells of myeloma cells and mammalian animal cells immunized with human adenocarcinoma cells, and a method for immuno-chemical determination of said specific antigen in sera by the use of said monoclonal antibody.

In recent years, there has been developed a process for preparation of a monoclonal antibodies in a large quantities which comprises cultivating hybridoma cells obtained by cell fusion of antibody-producing cells with myeloma cells (Milstein et al.: Nature, 256, 495-497 (1975)). The monoclonal antibody to a cancer-related antigen obtained by the process as disclosed in this literature can be used not only for analysis of the cancer-related antigen itself but also for detection of the antigen in serum, radioimmuno-imaging diagnosis, etc. due to its high specificity and uniformity.

Hitherto, there have been reported some processes for preparation of a monoclonal antibody to human lung carcinoma. However, the reports relating to an antibody having a specificity to adenocarcinoma are few, and the successful detection of any antigen in blood has never been reported. Recently, Iguro et al. reported that the monoclonal antibody CSLEXI prepared for stomach cancer cells is effective in detection of an antigen in sera of patients bearing cancers such as lung carcinoma (Lancet, 6, 817-818 (1984)), but the molecule of such antigen has not sufficiently been analyzed. Further, the antibody has a cross-reactivity with normal cells such as multinuclear leukocytes, liver cells and Kupffer cells other than cancer cells so that it is hardly usable for diagnosis of human cancers.

The monoclonal antibody 19-9 as ascertained by Koprowski et al. can recognize a blood group-related antigen (Somatic Cell Genetics, 3, 952-972 (1979)) and is used clinically for detection of a novel tumor marker. However, this antibody is positive not only to pancreas cancer and stomach cancer but also to colon cancer (59%). Among lung cancers, it is reactive to squamous epithelium carcinoma (3 cases in 4 cases) and small cell carcinoma (4 cases in 9 cases) in addition to adenocarcinoma. Thus, it is not specific to adenocarcinoma.

As a result of extensive study, there has now been successfully obtained a monoclonal antibody which is specifically reactive to adenocarcinoma such as lung adenocarcinoma, stomach adenocarcinoma and pancreas adenocarcinoma and hardly reactive to non-adenocarcinoma such as squamous epithelium carcinoma, large cell carcinoma and small cell carcinoma as well as normal cells. It has also been found that the diagnosis of various adenocarcinoma can be successfully carried out by immuno-chemical measurement of the specific antigen leaked out into the blood with said antibody.

According to the present invention, there is provided a monoclonal antibody having a specific reactivity to human adenocarcinoma cells, said antibody being produced from hybridoma cells obtainable by cell fusion of myeloma cells and mammalian animal cells immunized with human adenocarcinoma cells. Quite surprisingly, the specific antigen corresponding to said antibody leaks out into the blood from various adenocarcinoma cells. It is therefore possible to make the diagnosis of various cancers by immuno-chemical measurement of the specific antigen in the blood with said antibody. Further, said antibody is characteristic in reacting specifically with human adenocarcinoma cells and can, for instance, react with human lung cancer cells, especially lung adenocarcinoma. The antibody is thus useful for distinguishing various lung cancers. Furthermore, the blood level of the antigen corresponding to said antibody increases with the progress of the symptomatic stage of lung cancer so that the antibody can be used for investigation of the progressive degree of the cancer.

As stated above, the monoclonal antibody of the invention is not only useful as a reagent for the biochemical and pathological study of various cancers but also useful as a diagnostic agent for various cancers by clinical measurement of specific antigen in the sera of patients. Further, said antibody may be labeled with a radioactive isotope such as technetium-99 m or indium-111. Its administration to patients, followed by application of immuno-detection thereto according to the nuclear medical procedure makes the morphological diagnostic imaging of various cancers possible. Furthermore, said antibody may be conjugated with a radioactive isotope (e.g. iodine-131, yttrium-90) or a cytotoxic agent. Its administration to patients would produce a therapeutic effect.

Preparation of the monoclonal antibody according to the present invention will be hereinafter explained in detail.

For attaining this object, it is necessary first to produce hybridoma cells by cell fusion of antibody-producing cells with myeloma cells, and this can be done by a per se conventional procedure such as the Milstein et al. method as hereinabove stated.

The antibody-producing cells can be obtained by immunizing mammalian animal cells with human lung adenocarcinoma cells as the antigen. The human lung adenocarcinoma cells are not limitative, and any cultured human lung adenocarcinoma cells as already ascertained may be used. Especially preferred are human lung adenocarcinoma A549 cells. The mammalian animal cells are also not limitative, and their selection may be made appropriately taking into consideration their adaptability with myeloma cells used for cell fusion. In general, murine cells are used for this purpose. Immunization may be carried out by a per se conventional procedure. For instance, human cancer cells are diluted with a physiological saline solution and optionally admixed with Freund's complete adjuvant to make a suspension, which is administered intracutaneously into animals. Administration is effected several times at appropriate intervals. On day 3 or 4 after the last administration, animals having a high antibody titer are chosen, and the spleen cells are taken out for the use as the immuno-competent cells, i.e. antibody-forming or antibody-producing cells.

The thus produced antibody-producing cells and the myeloma cells are subjected to cell fusion. As the myeloma cells, there may be employed various ones chosen from P3/X63-Ag8, X63-Ag8.653, P3/X63-Ag-8.U1, P3/NS1-1-Ag4-1, SP2/0-Ag14, FO, MPC11-45.6TG1.7, etc. The cell fusion may be accomplished by a per se conventional procedure, for instance, by mixing together the antibody-producing cells and the myeloma cells as cultured in appropriate culture media, followed by stirring, shaking and/or centrifuging. If necessary, feeder cells chosen from thymus cells, abdominal cavity exuding cells, spleen cells and the like, fusion promoting agents such as polyethylene glycol, etc. may be added thereto. The culture medium may be any one as conventionally employed for cell culture, and its examples are an MEM culture medium, an RPMI-1640 culture medium, etc.

The thus obtained hybridoma cells are cultivated in a conventional medium for selection of hydridoma such as an HAT medium so as to obtain the desired hybridoma cells. Since the myeloma cells are deficient in hypoxanthin-guanine-phosphoribosyl transferase, they can not grow in the HAT medium. Further, the cells other than the desired hybridoma cells between the antibody-producing cells and the myeloma cells, such as the non-fused cells and the hybridoma cells of the antibody-producing cells can live in the HAT medium only for about 2 weeks. Accordingly, only the desired hybridoma cells can be recovered from the HAT medium after cultivation therein over a certain period of time. The recovered hybridoma cells are then subjected to collection of the antibody-producing strain and cloning by a conventional limiting dilution method.

The resultant monoclonal antibody-producing hybridoma cells can be cultivated successively in a conventional culture medium. Also, they can be stored in liquid nitrogen over a long period of time. The hybridoma cells producing the monoclonal antibody YH206 (hereinafter referred to as "hybridoma YH206") are stored and retained by the inventors themselves and can be freely obtained from them.

Examination as to whether the hybridoma YH206 can produce the monoclonal antibody (hereinafter referred to as "monoclonal antibody YH206") may be effected by any per se conventional antibody-detecting procedure such as the indirect immuno-fluorescent method, the indirect immuno-peroxidase method, the enzyme antibody method (enzyme-linked immunosorbent assay (ELISA)) or the radioimmunoassay method.

For production of the monoclonal antibody YH206 with the hybridoma YH206 cells, those hybridoma cells may be subjected to tissue culture, followed by collection of the culture supernatant. Alternatively, the hybridoma cells may be administered intraperitoneally to animals having the adaptability thereto for growth, and then the ascitic fluid may be collected therefrom. In the former process, the antibody having a high purity is obtainable. In the latter process, the antibody can be produced on a large scale. The collected supernatant or ascitic fluid may be purified by a method as conventionally employed for purification of proteins to give the desired monoclonal antibody YH206.

The immuno-histological diagnosis with the monoclonal antibody YH206 and the diagnosis of cancer by measurement of the corresponding specific antigen (tumor marker) in the body fluid will be hereinafter explained.

Various cancer tissues are fixed with formalin and embedded in paraffin, followed by slicing. With the resulting specimens, the immuno-peroxidase method such as the anti-peroxidase complex method or the avidin-biotin-peroxidase complex method is effected, whereby the histological diagnosis of cancer can be readily accomplished within a short period of time without the complex procedure required for conventional pathologic histological observation.

The diagnosis of various cancers can be also accomplished by utilization of the specific antigen corresponding to the monoclonal antibody YH206, said antigen being leaked out from the cancer cells into the body fluid. For instance, the quantity of the specific antigen exuded from the cancer cells into the body fluid may be determined by immunoassay with the monoclonal antibody YH206, and the diagnosis of cancer is made from the obtained results. As the immunoassay, there may be adopted the reversed passive hemagglutination method, the enzyme immunoassay method, the fluoroimmunoassay method, the radioimmunoassay method or the like.

Practical and presently preferred embodiments of the invention are illustratively shown in the following Examples.

EXAMPLE 1

Preparation and screening of the hybridoma YH206:

Into each of BALB/c mice, human lung adenocarcinoma A549 cells ($1 \times 10^7$) were intraperitoneally administered 4 times with intervals of 2 weeks. On the third day after the last immunization, the spleen was taken out. Spleen cells ($1 \times 10^8$) and murine myeloma X63-Ag8.653 cells ($1 \times 10^7$) were subjected to cell fusion by the use of polyethyleneglycol (molecular weight, 1500) as the fusion promoting agent. The above cells were cultivated in a HAT culture medium (RPMI 1640 culture medium containing hypoxanthine, aminopterin, thymidine and 10% fetal calf serum) in a culture plate of 96 holes. After 1 week, the HAT culture medium was exchanged with a fresh one (50 μl) once every 3 days. After 2 to 3 weeks, 280 clones were observed in 400 wells. Screening was carried out using the supernatants from these 280 wells.

Screening was effected by application of the indirect immuno-fluorescent antibody method and the indirect immuno-peroxidase method. The former method was performed by the use of the hybridoma supernatant as the primary antibody and the FITC labeled rabbit anti-mouse immuno-globulin as the secondary antibody, and the reactivity with human lung adenocarcinoma A549 was investigated by the aid of a fluorescent microscope. Among the hybridoma cells associated with human lung adenocarcinoma A549 cells as used in immunization, the hybridoma YH206 cells strongly reactive to lung adenocarcinoma on a tissue slice were chosen and subjected to cloning twice.

The latter method was performed by fixing the tissue materials obtained from various cancers and fetal tissues with 10% formalin, embedding the fixed specimens in paraffin, selecting lung adenocarcinoma, lung alveolar cell carcinoma, lung epidermoid carcinoma and lung large cell carcinoma and normal lung from the embedded specimens and examining their reactivity according to the Watanabe et al. method ("Enzyme Antibody Method, Theory-Operation, Explanation and its Application", pages 33-39 (1984)).

EXAMPLE 2

Preparation of the monoclonal antibody YH206:

Cloning hybridoma YH206 was cultivated in a cell culture flask, and the supernatant was collected. On the other hand, the cells of said hybridoma ($1 \times 10^7$) were intraperitoneally administered to BALB/c mice previously administered with pristane (2,6,10,14-tetramethylpentadecane), and after about 2 weeks, the ascitic fluid was collected. Said supernatant and said ascitic fluid were salted out with ammonium sulfate and purified by gel filtration with Sephacryl S-300.

EXAMPLE 3

Determination of the immunoglobulin class of the monoclonal antibody YH206:

The immunoglobulin sub-class of the monoclonal antibody YH206 was determined to be IgM according to the Ouchterlony method by the use of rabbit anti-mouse IgG1, IgG2a, IgG2b, IgG3, IgA and IgM (Miles Lab.).

EXAMPLE 4

Examination of the tissue distribution of the antigen corresponding to the monoclonal antibody YH206:

Using the monoclonal antibody YH206 as obtained in Example 2, the tissue distribution of the corresponding antigen was examined on various human cancer tissues, normal human adult tissues and fetal tissues.

Each tissue was fixed with 10% formalin, embedded in paraffin and sliced to make a specimen of 4 to 5 μm in thickness, followed by storage at 4° C. The specimen was subjected to hematoxylin-eosin staining and then histologically examined. Thereafter, the indirect immuno-peroxidase method was applied thereto according to said Watanabe et al. method. Namely, the endogenous peroxidase activity of the specimen was removed by treatment with 0.6% hydrogen peroxide-methanol. Normal rabbit serum was reacted thereto for inhibiting the non-specific adsorption of the secondary antibody. The monoclonal antibody as the primary antibody and then the peroxidase-labled rabbit anti-mouse immunoglobulin were reacted thereto. Coloring was effected by the use of 3,3'-diaminobenzidine. Nuclear staining was carried out with 0.2% methylgreen.

The results are shown in Tables 1 and 2.

TABLE 1

Tissue distribution of the antigenic determinant recognized by the monoclonal antibody YH206
(A) Cancer tissues

| Organ | Type | Staining property | |
|---|---|---|---|
| Lung | adenocarcinoma | ++(*) | (9/13)(**) |
| | alveolar cell carcinoma | ++ | (2/2) |
| | epidermoid carcinoma | F+ | (1/6) |
| | large cell carcinoma | F+ | (1/5) |
| | small cell carcinoma | — | (0/6) |
| Pancreas | adenocarcinoma | ++ | (3/4) |
| Stomach | adenocarcinoma | + | (6/9) |
| | singnet-ring cell carcinoma | — | (0/3) |
| Liver | cholangiocarcinoma | + | (1/1) |
| | hepatocellular carcinoma | — | (0/2) |
| Breast | scirrhous carcinoma | — | (0/2) |
| Colon | adenocarcinoma | — | (0/10) |
| Kidney | Grawitz's tumor | — | (0/1) |
| Gall bladder | adenocarcinoma | — | (0/1) |

(*)Staining intensity: ++, strongly positive; +, positive; F+, faintly positive; —, negative.
(**)Number of positive/number of tested.

TABLE 2

Tissue distribution of the antigenic determinant recognized by the monoclonal antibody YH206
(B) Normal tissues

| Organ | Adult | | Fetus | |
|---|---|---|---|---|
| Lung | —(*) | (0/8)(**) | ++ | (1/1) |
| Colon | — | (0/9) | + | (1/1) |
| Kidney | F+ | (3/4) | ++ | (1/1) |

TABLE 2-continued

Tissue distribution of the antigenic determinant recognized by the monoclonal antibody YH206
(B) Normal tissues

| Organ | Adult | | Fetus | |
|---|---|---|---|---|
| Liver | — | (0/4) | + | (0/1) |
| Pancreas | F+ | (3/3) | F+ | (1/1) |
| Small intestine | — | (0/4) | + | (1/1) |
| Stomach | — | (0/8) | n.t.(***) | |
| Adrenal gland | — | (0/1) | n.t. | |
| Brain | — | (0/1) | n.t. | |
| Esophagus | — | (0/2) | n.t. | |
| Heart | — | (0/1) | n.t. | |
| Lymphnode | — | (0/2) | n.t. | |
| Skeltal muscle | — | (0/1) | n.t. | |
| Spinal cord | — | (0/1) | n.t. | |
| Spleen | — | (0/2) | n.t. | |
| Thyroid gland | — | (0/1) | n.t. | |

(*)Staining intensity: ++, strongly positive; +, positive; F+, faintly positive; —, negative.
(**)Number of positive/number of tested.
(***)Not tested.

In the case of lung cancers, a relatively limited reactivity to adenocarcinoma and alveolar cell carcinoma was indicated, and 11 cases were positive in 15 cancers. The staining pattern of the adenocarcinoma was a labeling of the apical surface of tumor cell, while that of the lung epidermoid carcinoma was cytoplasmic. In the case of large cell carcinoma, staining property was recognized in one of 5 cases, but its observation was limited to a part of cancer cells. In the case of small cell carcinoma, no positive reaction was observed. In the case of other organ carcinomas, positive reaction was observed in 3 cases of 4 pancreas cancers, 6 cases of 9 stomach cancers and 1 case of 1 gall bladder cancer. In stomach adenocarcinoma, most cases were positive in an apical surface and also in secreted products with a tendency that mucin lake is strongly stained. On the other hand, stomach signet-ring cell carcinoma (0/3), liver hepatocellular carcinoma (0/2), large intestine carcinoma (0/10), kidney cancer (0/1), breast cancer (0/2) and gall bladder adenocarcinoma (0/1) gave no reactivity.

As shown in Table 2, the examination of the non-malignant tissues of human adults revealed that extremely limited reaction is slightly recognized with renal tubule and extrapancreatic secreting gland. In the lung tissue, no reaction was observed with any of alveolar epithelium, bronchial epithelium and tracheal mucous gland. Distribution of the antigen in the fetal tissue was so broad as including lung, and the staining property was strong in comparison with that in the adult tissue.

As understood from the above, the antigen distribution is limited to adenocorcinoma and alveolar carcinoma in the lung tissue, while it extends to stomach cancer and pancreas cancer with high frequency among other tissues. In the non-malignant adult tissue, weak reaction was observed only with very small portions of renal tubule epithelium and extrapancreatic secreting gland, and detection was not made from any normal lung tissue. The antigen distribution in the fetal tissue extends to a relatively broad area, and reactivity is observed in stomach, large intestine and lung where the antigen is not detected in case of the adult tissue. The antigen is thus detected mainly in adrenocarcinoma and the fetal tissues and only in trace from the normal adult tissues. From such characteristic distribution, it may be said that the antigen corresponding to the monoclonal antibody YH206 is like carcinoembryonic antigen (CEA).

EXAMPLE 5

Reactivity of the monoclonal antibody YH206 with erythrocytes:

A 2% suspension of human erythrocytes $A_1$, $A_2$, B or O (Ortho Diagnostics) was prepared, and the reactivity with the monoclonal antibody YH206 was examined with the hemagglutination according to the physiological saline solution method, the albumin method and the indirect Coombs' test. As the positive control, the anti-H (type 2) monoclonal antibody S1 was used. Further, the reactivity with neuraminidase-treated erythrocytes was examined by the Rahman-Longenecker method.

Namely, neuraminidase (Sigma No. N-2876) was added to a 5% erythrocyte suspension in an amount of 0.5 µ/ml, and incubation was effected at 37° C. for 1 hour. After washing with PBS (phosphate buffered saline), it was used in the form of a 2% suspension. As the positive control, the Thomsen-Friedenreich antigen-monoclonal antibody 49H.8 was used. The antibody was used by adjusting the purified product to a concentration of 5 µg/ml.

As the result, the monoclonal antibody YH206 did not produce any hemagglutination with any of the erythrocytes, and no correlation to any of the A, B and H-type antigens was observed. Also, no agglutination with the neuraminidase-treated erythrocytes was produced.

EXAMPLE 6

Chemical properties of the antigen corresponding to the monoclonal antibody YH206 - periodic acid oxidation of tissue strips:

According to the known method as described in Kiernan: "Histological and Histo-chemical Methods—Theory and Practice", pages 153-156 (1981), each of the tissue strips from various organs after removal of the endogeneous peroxidase activity was reacted with 1% periodic acid solution at room temperature for 10 to 20 minutes, followed by staining as in Example 4.

As the result, it was observed that the tissue having a reactivity with the monoclonal antibody YH206 loses the reactivity with the corresponding antigen completely when oxidized with periodic acid. This fact suggests that the antigenic determinant of the antibody is a sugar chain.

EXAMPLE 7

Chemical properties of the antigen corresponding to the monoclonal antibody YH206 - neuraminidase digestion of tissue strips:

In order to investigate whether sialic acid participates in the antigenic determinant, observation was made on the reactivity of the tissue strips with the monoclonal antibody YH206, said tissue strips consisting of 13 malignant tissues and 8 non-malignant tissues giving positive or negative in the immuno-peroxidase method previously digested with neuraminidase. Neuraminidase digestion was carried out according to the Atkinson et al method. Namely, the tissue strips after removal of the endogenous peroxidase activity were treated with neuraminidase (Sigma No. N-3001) (1 µ/ml; 0.1M acetate buffer of pH 5.11) at 37° C. for 12 hours, washed well with PBS and subjected to immuno-peroxidase staining. For the tissue strips as the control, 0.1M acetate buffer not containing neuraminidase was used.

As the result, the decrease of the intensity or frequency of the staining positivity after neuraminidase digestion was not observed. Rather, the increase of staining with neuraminidase treatment was observed in some cases. In 12 cases of lung cancer, stomach cancer and large intestine cancer, the antibody not detected before treatment was sometimes detected after neuraminidase digestion. The lung alveolar cell carcinoma which was negative before treatment showed positive after neuraminidase digestion. The lung large cell carcinoma from which the corresponding antigen was not detected by the immuno-peroxidase method showed the remarkable presence of the antigen-positive cells after neuraminidase digestion, and this phenomenon was also observed in lung epidermoid carcinoma. The similar tendency to the above was also observed in 3 cases among 8 non-malignant tissues. In the gastric mucosa after neuraminidase digestion, the antibody showed reactivity to the gastric glands as well as the gastric epithelium. From these facts, it may be said that in at least some of the malignant and non-malignant tissues, the antigen is masked with sialic acid and becomes non-masked on treatment with neuraminidase.

This can be confirmed not only by the test with the tissue strips but also by the test with non-fixed cultured cancer cells. Accordingly, the antigenic determinant may be considered to be present in a cryptic form at the non-cancerous parts and masked with sialic acid. At the cancerous parts, the antigenic determinant is disclosed as such so that the monoclonal antibody may be detected with high frequency.

EXAMPLE 8

Chemical properties of the antigen corresponding to the monoclonal antibody YH206 - inhibition test of tissue strips with lectins:

For investigation of the antigen determinant, inhibition test was effected by the use of various lectins.

According to the known method as described in Hirano: "Histological Chemistry 1981—histological application of lectins", pages 17-39 (1982), each of biotinated lectins such as *Ulex europeus, Canavalia ensiformis, Ricinus communis, Triticum vulgaris, Dolichos biflorus* and *Arachis hypogaea* (Vector Labs.) was adjusted to a concentration of 50 µg/ml and subjected to reaction with tissue strips for 30 minutes. The reactivity of the monoclonal antibody was investigated as in Example 4.

As the result, any of the lectins as used could not completely block the reaction of the monoclonal antibody YH206. But, wheat-germ aggulutinin showed slight decrease of the reactivity of YH206.

The above fact suggests that a sugar portion (N-acetylglucosamine or sialic acid) reactive to WGA may be present in the antigenic determinant.

EXAMPLE 9

Chemical properties of the antigen corresponding to the monoclonal antibody YH206 - enzymatic treatment of cultured cells:

It was investigated whether the decrease or disappearance of the antigen determinant is caused by treatment with a protease such as tripsin or protease V 8. Namely, cultured cells ($2 \times 10^6$) of lung adenocarcinoma A549 were suspended in an RPMI 1640 culture medium (1 ml) and reacted with any enzyme solution (1 ml) as hereinafter mentioned at 37° C. for 1 hour. Then, a 10% FCS added RPMI 1640 culture medium (8 ml)

was added thereto to stop the reaction, washed well with RPMI and subjected to observation on the reactivity with the monoclonal antibody according to the indirect immunofluorescent antibody method. As said enzyme solution, there were used the ones chosen from the following five kinds: neuraminidase F (Seikagaku Kogyo) (0.1 μ/ml), protease V 8 (Miles) (0.5 mg/ml), trypsin (Warsinton) (0.5 mg/ml), glycosidase (mixed) (Seikagaku Kogyo) (2 mg/ml) and endoglycosidase H (Seikagaku Kogyo) (0.1 μ/ml). No decrease or disappearance of the antigen determinant was observed by treatment with any of the above five kinds of enzymes. This fact supports that the antigen determinant may be a sugar chain.

EXAMPLE 10

Detection and immunochemical investigation of the corresponding antigen in the lung adenocarcinoma supernatant:

Extraction of the crude antigen:

A549 cell ($1 \times 10^7$) were cultivated in a low concentration (1%) FCS added culture medium (HAM culture medium (Flow Laboratories), 50%; RPMI 1640 (Difco), 50%; hepes (Sigma), 20 mM; penicillin, 100 mg/liter; kanamycin, 50 mg/liter; sodium bicarbonate, 1 g/liter; insulin (Sigma), 5 mg/liter; transferrin (Sigma), 35 mg/liter; phosphatidylethanolamine (Sigma), 0.5 mg/liter; sodium selenite, $4.3 \times 10^3$ mg/liter) (70 ml) for 3 days. The supernant was collected several times and used as a crude antigen. From cultured lung cancer A549 cells and large intestine cancer BM314 cells, the crude antigen was extracted with 1% NP 40 (Nakarai Chemical) according to the freezing and thawing method. For fetal faeces, 1% NP 40 was used.

Enzyme antibody method:

The culture supernatant prepared according to the Magnani et al. method (J. Biol. Chem., 257, 14365–14369 (1982)) was concentrated to make a 2.5 fold, 10 fold, 20 fold or 40 fold concentration, which was admitted into a round bottom microplate (Falcon) in an amount of 50 μl/well and reacted at 37° C. for 12 hours. After blocking with 3% bovine serum albumin, the monoclonal antibody was reacted thereto. Then, peroxidase-conjugated rabbit anti-mouse immunoglobulin was reacted thereto, coloring was made with o-phenylenediamine, and absorbance was measured at 492 nm.

SDS-PAGE and western blotting:

The operation was carried out according to the Imai et al. method (Cancer Research, 41, 1028–1033 (1981)). As the gel, 5% or 10% gel was used. The antigen (50 μl) was developed with SDS-PAGE, transferred from the gel to the nitrocellulose membrane (pore size, 0.45 μ) according to the Watanabe et al. method ("Immunological Experimental Operations", 11, 3485–3489 (1982)) and detected with the indirect enzyme antibody method.

Gel-filtration:

As the gel, there was used Sephacryl S-300 (2.4 cm × 80 cm). On each fraction obtained by the use of the antigen (3 ml) as the starting material, the reactivity with the monoclonal antibody was measured according to the enzyme antibody method. For detection of the antigen in the supernatant of A549 cells, the enzyme antibody method using the antibody YH206 was applied. As the result, it was revealed that, in the supernatant of A549 cells, the antigen molecule reactive to YH206 is present. The supernatant was subjected to gel filtration using Sephacryl S-300, and the reactivity of the antigen of each fraction was measured by the enzyme antibody method. As the result, the antigen was detected around the void volume.

Then, the molecular weight of the corresponding antigen was investigated using A549 cells, CEA-producing large intestine cancer BM314 cells and fetal faeces as the crude antigen. As the control of the antibody, the anti-CEA monoclonal antibody AS802 was used. AS802 showed the reaction with fetal faeces and CEA-producing large intestine cancer BM314 cells at the position of about 200K dalton. On the other hand, YH206 showed the reaction with fetal faeces in three bands at the position of a higher molecule than CEA but did not show any significant reaction with the antigen obtained by extraction of the immunogen A549 with NP40.

Then, the analysis was made on the antigen obtained by extraction from A549 cells by the freezing and thawing method and the A549 supernatant as the crude antigen in the same manner as above. When the extraction was effected by the freezing and thawing method or when the A549 supernatant was used as the crude antigen, a clear single band was observed at the position of such a high molecule as more than 330K dalton.

Thus, the presence of an antigen in the A549 supernatant was shown by the enzyme antibody method, and SDS-PAGE and western blotting were effected with the antigen so that its molecular weight was revealed to be more than 330K dalton. Further, the reactivity of the antigen of each fraction obtained by gel filtration with Sephacryl S-300 was measured by the enzyme antibody method, and the antigen was detected around the void volume. Also, fetal faeces were analyzed by SDS-PAGE and western blotting, and three bands were observed at the position of a higher molecule than CEA; these are different from the antigen in the supernatant with respect to the molecular weight.

EXAMPLE 11

Detection of the antigen in a blood stream:

Since the antigen is present in the supernatant of the culture medium, it is expected that the antigen may be also present in a blood stream. The serum of a cancer patient was thus examined according to the RPHA (reversed passive hemagglutination) method.

The RPHA method was performed as reported by Iguro et al. (Lancet, 6, 817–818 (1984)). Namely, inactivated serum was absorbed with sheep red blood cells (SRBC) (room temperature, 1 hour) and serially diluted with PBS. The resulting dilutions were each added to a round bottom macro-titer plate (Sanko Pure-Chemical) in an amount of 30 μl per well. An equal quantity of a 2% suspension of SRBC associated with the monoclonal antibody with chromium chloride was added thereto, allowed to stand at room temperature for 4 hours and then subjected to observation on the hemagglutination. By previous addition of the monoclonal antibody to the serum or the antigen solution prepared as in Example 10, it was confirmed that the hemagglutination of SRBC is inhibited with a dependency on the antigen concentration.

As the test sera, there were used a total of 178 cases comprising 30 cases of normal control, 67 cases of lung cancer, 20 cases of stomach cancer, 15 cases of pancreas cancer, 15 cases of large intestine cancer and 31 cases of benign diseases (pneumonia, 5 cases; chronic hepatitis, 6 cases; liver cirrhosis, 7 cases; chronic articular rheumatism, 2 cases; peptic ulcer, 11 cases).

For the fundamental examination, a concentrate of the supernatant of the culture of A549 was used as the antigen, and hemagglutination was observed even when diluted to 4096 folds. Then, the above antigen was serially diluted and reacted with the antibody YH206, followed by hemagglutination. As the result, it was confirmed that the hemagglutination value was confirmed to be inhibited depending on the amount of the antibody as added. Similar results were obtained when the patient serum was used as the antigen.

On the basis of the above fundamental examination, the antigen in the blood taken from each of the patients bearing cancers was measured by the RPHA method. The level of the dilution of the serum for antigen positive was tentatively decided to be 1/64 dilution or more. In 30 healthy donors, three sera (10%) had antigen levels of 1/64 dilution. In contrast, among 67 patients with lung cancer, 35 sera (52.2%) showed positive. Further, 9 sera (45%) in 20 patients with stomach cancer, 11 sera (73.3%) in 15 patients with pancreas cancer and 9 sera (60%) in 15 patients with colon cancer indicated positive. When the sera from patients bearing no cancer were used, 4 sera (12.9%) in 31 patients, i.e. 2 sera in 7 patients with liver cirrhosis and 2 sera in 5 patients with acute pneumoniae (CRP being not less than 5+), were positive; all of 6 patients with chronic liver hepatitis, 2 patients with chronic articular rheumatism and 11 patients with peptic ulcer were negative; and in positive cases, hemagglutination was observed so low as 64 fold (1/64 dilution).

Observation on the sera from patients with lung cancer, of which the histological type was previously clarified, gave positive results for 13 cases (61.9%) in 21 adenocarcinoma, 6 cases (40%) in 15 epidermoid carcinoma, 8 cases (50%) in 16 small cell carcinoma and 3 cases (75%) in 4 large cell carcinoma.

Since SRBC was used as the indicater cells, the Forssman antibody therein might be detected. Therefore, the absorption with SRBC was previously applied. In case of sera having a high hemagglutination activity, it was confirmed that no hemagglutination would not take place with SRBC associated with YH206.

Summarizing the above results, it may be noted that while weak positive reaction is observed only in 3 cases among 30 healty donors, the percentage of positivity in various cancer patients is so high as 45 to 75% and the titers are relatively high in most cases.

From the above results, it is thus clear that the antibody of the invention is useful as a reagent for immunoassay of the corresponding antigen in a body fluid, particularly for diagnosis of various cancers.

EXAMPLE 12

Relationship to the clinical symptomatic stage of lung cancer:

With the lung cancer of which the clinical symptomatic stage is previously clarified, the amount of the antigen in blood was examined. The positivity percentage of the progressive cancers at the stages III and IV (73.3% and 62.5%) was higher than that at the stage I (22.2%). Further, the increase of the antigen amount in the former was higher than that in the latter.

Human lung adenocarcinoma cell line A549 and hybridoma YH206 have been deposited under the terms of the Budapest Treaty with the Fermentation Research Institute, Agency of Industrial Science and Technology, Ibaragi-ken, Japan and have respectively assigned Accession Numbers FERM BP-2000 and FERM BP-2001.

The deposit of A549 and the deposit of YH206 were both made on Aug. 16, 1988.

What is claimed is:

1. A cell line having all the identifying characteristics of YH206.

2. A monoclonal antibody produced by the YH206 cell line.

* * * * *